(12) United States Patent
Fourre et al.

(10) Patent No.: US 9,326,924 B1
(45) Date of Patent: *May 3, 2016

(54) COMPOSITIONS COMPRISING COMBINATIONS OF ORGANIC ACIDS

(71) Applicant: JOHNSON & JOHNSON CONSUMER INC., Skillman, NJ (US)

(72) Inventors: Tara Fourre, Columbia, NJ (US); Robert J. Gambogi, Hillsborough, NJ (US); Patricia L. Golas, North Brunswick, NJ (US); Anthony R. Geonnotti, III, Princeton, NJ (US); Benjamin Serbiak, Brooklyn, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,447

(22) Filed: Feb. 26, 2015

(51) Int. Cl.
*A61K 8/362* (2006.01)
*A61Q 11/00* (2006.01)
*A61K 8/365* (2006.01)
*A61K 8/92* (2006.01)

(52) U.S. Cl.
CPC ............. *A61K 8/362* (2013.01); *A61K 8/365* (2013.01); *A61K 8/922* (2013.01); *A61Q 11/00* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 3,678,154 A | 7/1972 | Widder | |
| 3,737,533 A | 6/1973 | Moon | |
| 4,051,234 A | 9/1977 | Gieske | |
| 4,138,477 A | 2/1979 | Gaffar | |
| 4,661,341 A | 4/1987 | Benedict | |
| 4,775,525 A | 10/1988 | Pera | |
| 4,847,070 A | 7/1989 | Pyrz | |
| 4,994,262 A | 2/1991 | Charbonneau | |
| 5,190,747 A | 3/1993 | Sekiguchi | |
| 5,328,682 A | 7/1994 | Pullen | |
| 5,338,537 A | 8/1994 | White, Jr. | |
| 5,451,401 A | 9/1995 | Zerby | |
| 5,538,714 A | 7/1996 | Pink | |
| 5,622,689 A | 4/1997 | Lukacovic | |
| 5,626,838 A | 5/1997 | Cavanaugh, Jr. | |
| 5,670,138 A | 9/1997 | Venema | |
| 5,849,271 A | 12/1998 | Lukacovic | |
| 6,121,315 A | 9/2000 | Nair | |
| 6,416,745 B1 | 7/2002 | Markowitz | |
| 6,682,722 B2 | 1/2004 | Majeti | |
| 7,084,104 B2 | 8/2006 | Martin | |
| 7,087,650 B2 | 8/2006 | Lennon | |
| 7,417,020 B2 | 8/2008 | Fevola | |
| 2006/0013778 A1 | 1/2006 | Hodosh | |

FOREIGN PATENT DOCUMENTS

| | | | |
|---|---|---|---|
| GB | 741315 | | 11/1955 |
| JP | 2000-063250 | | 2/2000 |
| WO | WO 99/12517 A1 | | 3/1999 |
| WO | WO-2012-001347 | * | 1/2012 |
| WO | WO 2012/001347 | | 1/2012 |
| WO | WO-2013-072932 | * | 8/2013 |

* cited by examiner

*Primary Examiner* — Frederick Krass
*Assistant Examiner* — Celeste A Roney

(57) ABSTRACT

Provided are compositions comprising succinic acid, aconitic acid, and a carrier, wherein the succinic acid and aconitic acid are present in a ratio of from about 0.9:1 to about 40:1. Also provided are methods of disrupting a biofilm comprising applying to a surface having a biofilm a composition of the present invention.

20 Claims, 2 Drawing Sheets

COMPOSITIONS COMPRISING COMBINATIONS OF ORGANIC ACIDS

FIELD OF THE INVENTION

The present invention relates to compositions comprising combinations of organic acids and their uses. In certain embodiments, the present invention relates to compositions comprising combinations of succinic acid and aconitic acid and uses of such compositions for disrupting biofilms.

BACKGROUND OF THE INVENTION

Organic acids, and combinations thereof, have been identified for use in a wide variety of compositions, including in compositions for oral care. For example, International Publication No. WO2012/001347 describes oral health compositions comprising extracts from shiitake mushroom, chicory, and/or raspberry, and low-molar mass fractions derived from the extracts. These compositions as described may comprise, or may be supplemented, with one or more of the following compounds: quinic acid, adenosine, inosine, trans-aconitic acid, cis-aconitic acid, oxalic acid, adenosine, and succinic acid. While the reference claims anti-biofilm effects of its compositions via several mechanisms of action, it does not disclose any unexpected benefits resulting from any particular combinations of the above compounds.

SUMMARY OF THE INVENTION

Applicants have discovered unexpectedly that certain combinations of organic acids can be combined to make compositions that tend to exhibit significant and unexpected benefits, including increased biofilm disruption.

According to certain embodiments, the present invention relates to compositions comprising succinic acid, aconitic acid, and a carrier, wherein the succinic acid and aconitic acid are present in a ratio of from about 0.9:1 to about 40:1.

According to certain other embodiments, the present invention relates to methods of disrupting a biofilm comprising applying to a surface having a biofilm a composition of the claimed invention.

According to certain other embodiments, the present invention relates to methods of removing a biofilm from a surface comprising applying to a surface having a biofilm a composition of the claimed invention.

According to certain other embodiments, the present invention relates to methods of reducing bacterial attachment to a surface comprising applying to the surface a composition of the claimed invention.

DETAILED DESCRIPTION OF THE INVENTION

Figure 1:
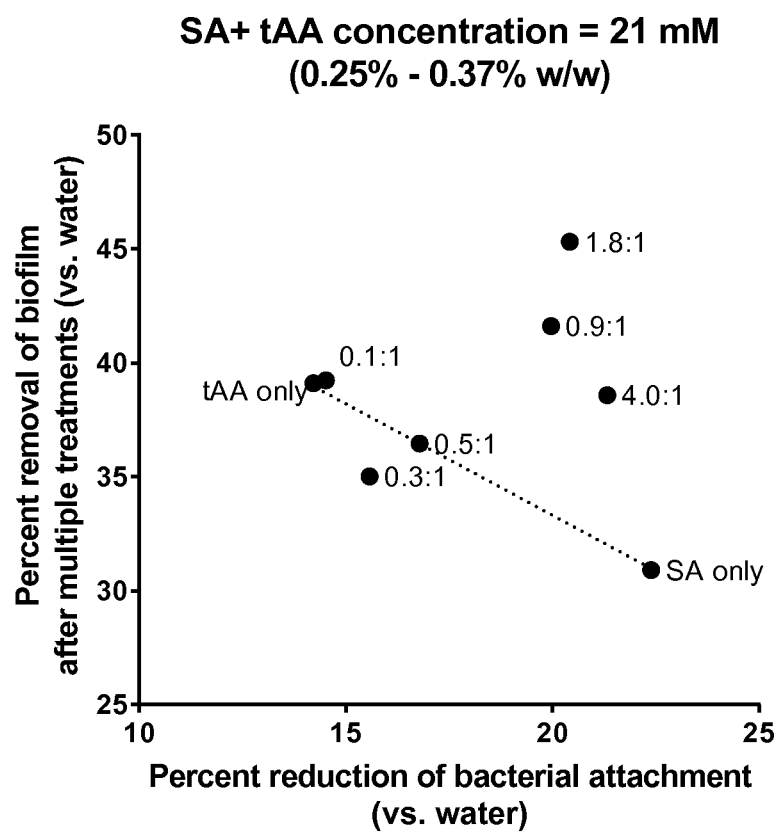
FIG. 1 is a plot of the percent removal of biofilm after multiple treatments (vs. water) versus percent reduction of bacterial attachment (vs. water) for formulations containing succinic acid (SA) and aconitic acid (AA) in varying ratios at a total concentration of 21 mM (0.25-0.37% w/w, depending on the ratio of SA to AA, see table 7).

All percentages listed in this specification are percentages of solids/active amounts by weight, unless otherwise specifically mentioned.

As noted above, applicants have discovered unexpectedly that compositions comprising combinations of both succinic acid and aconitic acid in a carrier tend to exhibit significant benefits over other combinations of organic acids. In particular, in certain embodiments, applicants have discovered that such compositions exhibit significant increase in disrupting biofilms. More specifically, as further described herein below and shown in the Tables and Figures, applicants have discovered that combinations of succinic acid and aconitic acid tend to exhibit significant increase in both (a) percent removal of biofilm and (b) percent reduction of bacterial attachment over other combinations of organic acids. Applicants note that as used herein "disrupting a biofilm" refers to removal of biofilm from a surface, reduction of bacterial attachment to a surface, or both.

Any suitable succinic acid may be used in the present invention. Succinic acid, also known by the IUPAC systematic name, butanedioic acid, or the historical name spirit of amber, is a diprotic, dicarboxylic acid with chemical formula $C_4H_6O_4$ and structural formula $HOOC-(CH_2)_2-COOH$. The succinic acid used herein may be naturally or synthetically derived. In certain embodiments, the succinic acid is synthetically derived. Commercially available sources of succinic acid include Acros Organics, Alfa Aesar, Fisher Chemical, Fluka, MP Biomedicals, Sigma Aldrich, Spectrum Chemicals, and TCI Fine Chemicals.

Any suitable aconitic acid may be used in the present invention. Aconitic acid, also known by the IUPAC systematic name, prop-1-ene-1,2,3-tricarboxylic acid, or the historical names Achilleic acid, Equisetic acid, Citridinic acid, or Pyrocitric acid, is an organic acid with chemical formula $C_6H_6O_6$ and structural formula $HO_2CCH=C(CO_2H)CH_2CO_2H$, and having two isomers cis-aconitic acid and trans-aconitic acid. In certain embodiments, the trans-aconitic acid is used. In other embodiments, the cis-aconitic acid is used. The aconitic acid used herein may be naturally or synthetically derived. In certain embodiments, the aconitic acid is synthetically derived. Commercially available sources of aconitic acid include Alfa Aesar, Fluka, MP Biomedicals, Parchem Fine & Specialty Chemicals, Sigma Aldrich, Spectrum Chemicals, and TCI Fine Chemicals.

Any suitable amounts and ratios of the succinic acid and aconitic acid may be used in the compositions of the present invention. As will be recognized by those of skill in the art, based on their respective pKa values, the succinic and aconitic acids used in the present invention will be in equilibrium with their respective salt forms at most pHs. Accordingly, all amounts and ratios of succinic and aconitic acid described and claimed herein refer to the total amount of such acid in both its acid and salt form in a particular composition. For example, a composition comprising 0.2% w/w of succinic acid has a total amount of combined solid/active succinic acid in its acid and salt forms of 0.2% w/w based on the total weight of the composition. A composition comprising a total combined amount of 1% w/w of succinic acid and trans-aconitic acid comprises a combined solid/active amount of succinic acid in its acid and salt forms and trans-aconitic acid in its acid and salt forms of 1% w/w based on the total weight of the compositions.

In certain embodiments, the succinic acid and aconitic acid are present in the composition in a total combined amount that is effective to prevent and disrupt biofilm formation in the oral cavity and at which the composition is stable. Generally, the composition contains succinic acid and aconitic acid in a total combined amount of from about 0.1 to about 2% by weight based on the total weight of the composition (% w/w). In certain embodiments, the total combined amount of succinic acid and aconitic acid is from about 0.1 to about 1% w/w of the composition, or from about 0.1 to about 0.9% w/w of the composition, or from about 0.1 to about 0.5% w/w of the composition, or from about 0.1 to about 0.3% w/w of the composition. In certain embodiments, the composition comprises a total combined amount of succinic acid and aconitic acid of from about 0.13% to about 0.89% w/w of the composition, from about 0.13% to about 0.52% w/w of the composition, or from about 0.13% to about 0.3% w/w of the composition.

Generally, the ratio of succinic acid to aconitic acid in the compositions of the present invention (succinic: aconitic) is from about 0.9:1 to about 40:1. In certain embodiments, the ratio of succinic acid to aconitic acid is from about 0.9:1 to about 20:1, or from about 0.9:1 to about 14:1, or from about 0.9:1 to about 9:1, or from about 0.9:1 to about 6:1, or from about 0.9:1 to about 4:1. In certain embodiments, the ratio of succinic acid to aconitic acid is from about 1.1:1 to about 20:1, or from about 2.5:1 to about 20:1, or from about 6:1 to about 20:1, or from about 1.1:1 to about 14:1, or from about 2.5:1 to about 14:1, or from about 6:1 to about 14:1, or from about 1.1:1 to about 9:1, or from about 2.5:1 to about 9:1, or from about 6:1 to about 9:1. In certain embodiments, the ratio of succinic acid to aconitic acid is from about 1.3:1 to about 20:1, or from about 1.3:1 to about 13:1, or from about 1.3:1 to about 8.33:1, or from about 1.3:1 to about 6:1, or from about 2.5:1 to about 13:1, or from about 2.5:1 to about 8.33:1, or from about 2.5:1 to about 6:1, or from about 6:1 to about 8.33:1, or from about 4:1 to about 5.5:1. In certain preferred embodiments, the ratio of succinic acid to aconitic acid from about 0.9:1 to about 14:1.

Any of a wide variety of orally-acceptable vehicles may be used in the present compositions. The vehicle can be aqueous or non-aqueous. The aqueous vehicle is generally water, although water/alcohol mixtures may also be employed. In certain embodiments, water is added to q.s. (Quantum Sufficit, Latin for "as much as needed") the composition. In certain embodiments, the aqueous phase comprises from about 60% to about 95%, or from about 75% to about 90%, by weight of the composition. In certain compositions, water is present in an amount of from about 60% to about 95%, or from about 75% to about 90%. Alternatively, the compositions of the present invention may be formulated in a dry powder, chewing gum, film, semi-solid, solid or liquid concentrate form. In such embodiments, for example, water is added to q.s. as necessary in the case of liquid concentrates or powdered formulations, or water may be removed using standard evaporation procedures known in the art to produce a composition in dry powder form. Evaporated, or freeze dried forms are advantageous for storage and shipping.

In some embodiments, alcohol may be added to the composition. Any of a variety of alcohols represented by the formula $R_3$—OH, wherein $R_3$ is an alkyl group having from 2 to 6 carbons, may be used in the present invention. Examples of suitable alcohols of formula $R_3$—OH include ethanol; n-propanol, iso-propanol; butanols; pentanols; hexanols, and combinations of two or more thereof, and the like. In certain embodiments, the alcohol is, or comprises, ethanol.

In some embodiments, the alcohol may be present in the composition in an amount of about 10.0% v/v or greater of the total composition, or from about 10.0% to about 35.0% v/v of the total composition, or from about 15.0% to about 30.0% v/v of the total composition and may be from about 20.0% to about 25.0% v/v of the total composition.

In some embodiments, the compositions may comprise a reduced level of alcohol. The phrase "reduced level" of alcohol means an amount of a $R_3$—OH alcohol of about 10% v/v or less, or about 5% v/v or less, or about 1.0% v/v or less, or about 0.1% v/v or less by volume of the total composition. In certain embodiments, the compositions of the present invention are free of $R_3$—OH alcohols.

The compositions of the present invention preferably have a pH of less than 7. In certain embodiments, the composition have a pH of from about 3 to less than 7, or from about 3.5 to less than 7, or from about 3.5 to about 6.5, or from about 3.5 to about 5.5, or from about 3.5 to about 5.

As will be recognized by those of skill in the art, the pH of the composition may be adjusted or achieved using a buffer in an amount effective to provide the composition with a pH below 7. The composition can optionally comprise at least one pH modifying agents among those useful herein include acidifying agents to lower pH, basifying agents to raise pH, and buffering agents to control pH within a desired range. For example, one or more compounds selected from acidifying, basifying and buffering agents can be included to provide a pH of about 2 to about 7, or in various embodiments from about 3 to about 6, or from about 4 to about 5. Any orally acceptable pH modifying agent can be used including without limitation carboxylic and sulfonic acids, acid salts (e.g., monosodium citrate, disodium citrate, monosodium malate, etc.), alkali metal hydroxides such as sodium hydroxide, borates, silicates, imidazole and mixtures thereof. One or more pH modifying agents are optionally present in a total amount effective to maintain the composition in an orally acceptable pH range. In certain embodiments, inorganic acids may be used as the buffer added to the composition.

In certain embodiments, organic acids may be used as the buffer added to the composition. Organic acids suitable for use in the compositions of the present invention include, but are not limited to, ascorbic acid, sorbic acid, citric acid, glycolic acid, lactic acid and acetic acid, benzoic acid, salicylic acid, phthalic acid, phenolsulphonic acid, and mixtures thereof, optionally, the organic acid is selected from the group consisting of benzoic acid, sorbic acid, citric acid and mixtures thereof, or optionally, the organic acid is benzoic acid.

Generally the amount of acidic buffer is between about 0.001% (or about 0.001% w/v) to about 5.0% (or about 5.0% w/v) of the composition. In certain embodiment, the organic acid buffer is present in amounts of from 0.001% (or about 0.001% w/v) to 1.0% w/v (or about 1.0% w/v) of the composition, or between about 0.100% (or about 0.100% w/v) to about 1.0% (or about 1.0% w/v) of the composition.

The compositions of the present invention may further comprise any of a variety of optional ingredients therein, including, but not limited to oily components, active ingredients, additional surfactants, humectants, solvents, flavors, sweeteners, colorants, preservatives, pH adjusters, pH buffers, and the like.

Any of a variety of oily components may be used in the present compositions. The oily component may comprise any one or more oils, or other materials that are water insoluble, or substantially water-insoluble, meaning that its solubility is less than about 1% by weight in water at 25° C. or, optionally, less than about 0.1%. In certain embodiments, the oily component of the present invention comprises, consists essentially of, or consists of, at least one essential oil, i.e. a natural or synthetic (or combination thereof) concentrated hydrophobic material of vegetable origin, generally containing volatile compounds, at least one flavor oil, or a combination of two or more thereof. Examples of suitable essential oils, flavor oils, and their amounts are described below. In certain embodiments, the composition comprises a total amount of oily component of about 0.05% w/w or more, about 0.1% w/w or more, or about 0.2% w/w or more of oily component.

In certain embodiments, compositions of the present invention comprise essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, avender oil, mustard oil, phenol, phenyl salicylate, pine oil, pine needle oil, sassafras oil, spike lavender oil, storax, thyme oil, tolu balsam, terpentine oil, clove oil, and combinations thereof.

In certain embodiments, the essential oils are selected from the group consisting of thymol (($CH_3$)$_2$CHC$_6$H$_3$(CH$_3$)OH, also known as isopropyl-m-cresol), eucalyptol ($C_{10}H_{18}O$, also known as cineol), menthol ($CH_3C_6H_9(C_3H_7)OH$), also known as hexahydrothymol), methyl salicylate ($C_6H_4OHCOOCH_3$, also known as wintergreen oil), isomers of each of these compounds, and combinations of two or more thereof. In some embodiments, the compositions of the present invention contain thymol. In some embodiments, the compositions of the present invention contain menthol. In some embodiments, the composition contains all four of these essential oils.

In certain embodiments, thymol is employed in amounts of from about 0.0001% to about 0.6% w/v, or from about 0.005% to about 0.07% w/v of the composition. In certain embodiments, eucalyptol may be employed in amounts of from about 0.0001% to about 0.51 w/v, or from about 0.0085% to about 0.10% w/v of the composition. In certain embodiments, menthol is employed in amounts of from about 0.0001% to about 0.25% w/v, or from about 0.0035% to about 0.05% w/v of the composition. In certain embodiments, methyl salicylate is employed in amounts of from about 0.0001% to about 0.28% w/v, or from about 0.004% to about 0.07% w/v of the composition. In certain embodiments, the total amount of all of such essential oils present in the disclosed compositions can be from about 0.0004% to about 1.64% w/v, or from about 0.0165% to about 0.49% w/v of the composition.

In certain embodiments, fluoride providing compounds may be present in the mouth rinse compositions of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium hexafluorosilicate, ammonium hexafluorosilicate, sodium fluorozirconate, sodium monofluorophosphate, aluminum mono- and difluorophosphate and fluorinated sodium calcium pyrophosphate. Amine fluorides, such as N'-octadecyl-trimethylendiamine-N,N,N'-tris(2-ethanol)-dihydrofluoride and 9-octadecenylamine-hydrofluoride), may also be used. In certain embodiments, the fluoride providing compound is generally present in an amount sufficient to release up to about 5%, or from about 0.001% to about 2%, or from about 0.005% to about 1.5% fluoride by weight of the composition.

In certain embodiments, sensitivity reducing agents, such as potassium salts of nitrate and oxalate in an amount from about 0.1% to about 5.0% w/v of the composition may be incorporated into the present invention. Other potassium releasing compounds are feasible (e.g. KCl). High concentrations of calcium phosphates may also provide some added sensitivity relief. These agents are believed to work by either forming an occlusive surface mineral deposit on the tooth surface or through providing potassium to the nerves within the teeth to depolarize the nerves. A more detailed discussion of suitable sensitivity reducing agents can be found in US 2006/0013778 to Hodosh and U.S. Pat. No. 6,416,745 to Markowitz et al., both of which are herein incorporated by reference in their entirety.

In certain embodiments, compounds with anti-calculus benefits (e.g. various carboxylates, polyaspartic acid, etc.) may be incorporated into the present invention. Also useful as an anticalculus agent are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 by weight copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available, for example, as Gantrez 25 AN 139 (M.W. 500,000), AN 119 (M.W. 250,000) and preferably S-97 Pharmaceutical Grade (M.W. 70,000), of GAF Chemicals Corporation.

Additional anti-calculus agents may be selected from the group consisting of polyphosphates (including pyrophosphates) and salts thereof polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; carboxy-substituted polymers; and mixtures thereof. In one embodiment, the salts are alkali metal or ammonium salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1,-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

In certain embodiments, zinc salts such as zinc chloride, zinc acetate or zinc citrate may be added as an astringent for an "antiseptic cleaning" feeling, as a breath protection enhancer or as anti-calculus agent in an amount of from about 0.0025% w/v to about 0.75% w/v of the composition.

Any of a variety of additional surfactants may be used in the present invention. Suitable surfactants may include anionic, non-ionic, cationic, amphoteric, zwitterionic surfactants, and combinations of two or more thereof. Examples of suitable surfactants are disclosed, for example, in U.S. Pat. No. 7,417,020 to Fevola, et al which is incorporated in its entirety herein by reference.

In certain embodiments, the compositions of the present invention comprise a non-ionic surfactant. Those of skill in the art will recognize that any of a variety of one or more non-ionic surfactants include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; alkyl glucose amines, block copolymers such as ethylene oxide and propylene oxide copolymers e.g. Poloxamers; ethoxylated hydrogenated castor oils available commercially for example under the trade name CRODURET (Croda Inc., Edison, N.J.); alkyl polyethylene oxide e.g. Polysorbates, and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

Exemplary non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25. By way of example, non-ionic surfactants useful in this invention include the poloxamers identified as poloxamers 105, 108, 124, 184, 185, 188, 215, 217, 234, 235, 237, 238, 284, 288, 333, 334, 335, 338, 407, and combinations of two or more thereof. In certain preferred embodiments, the composition comprises poloxamer 407.

In certain embodiments, the compositions of the claimed invention comprise less than about 9% of non-ionic surfactant, less than 5%, or less than 1.5%, or less than 1%, or less than 0.8, less than 0.5%, less than 0.4%, or less than 0.3% of non-ionic surfactants. In certain embodiments, the composition of the present invention is free of non-ionic surfactants.

In certain embodiments, the compositions of the present invention also contain at least one alkyl sulfate surfactant. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. A typical percentage breakdown of alkyl sulfates by alkyl chain length in commercially available sodium lauryl sulfate (SLS) is as follows:

Alkyl Component
Chain Percentage
Length in SLS
$C_{12}$ >60%
$C_{14}$ 20%-35%
$C_{16}$ <10%
$C_{10}$ <1%
$C_{18}$ <1%

In certain embodiments, the alkyl sulfate surfactant is present in the composition from about 0.001% to about 6.0% w/v, or optionally from about 0.1% to about 0.5% w/v of the composition.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, or from about 0.5% to about 2% by weight of the total composition.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alky lamphoglycinates (mono or di), alkylamphoproprionates (mono or di), alkylamphoacetates (mono or di), N-alkyl[3-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium auroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the compositions of the claimed invention comprise less than about 9% of amphoteric surfactant, less than 5%, or less than 1.5%, or less than 1%, or less than 0.8, less than 0.5%, less than 0.4%, or less than 0.3% of amphoteric surfactants. In certain embodiments, the composition of the present invention is free of amphoteric surfactants.

Additional surfactants may be added with the alkyl sulfate surfactant to aid in solubilization of the essential oils provided such surfactants do not affect the bioavailability of the essential oils. Suitable examples include additional anionic surfactants, nonionic surfactants, amphoteric surfactants and mixtures thereof. However, in certain embodiments, the total surfactant concentration (including the alkyl sulfate surfactant alone or in combination with other surfactants) for mouth rinses of the present invention should not exceed or should about 9% or less, optionally, the total surfactant concentration should be about 5% or less, optionally about 1% or less, optionally about 0.5% or less w/w % of active surfactant by weight of the composition.

In certain embodiments, a sugar alcohol (humectant) is also added to the oral compositions of the present invention. The sugar alcohol solvent(s) may be selected from those multi-hydroxy-functional compounds that are conventionally used in oral and ingestible products. In certain embodiments, the sugar alcohol (s) should be nonmetabolized and non-fermentable sugar alcohol (s). In specific embodiments, the sugar alcohols include, but are not limited to sorbitol, glycerol, xylitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. In some embodiments, the sugar alcohol is sorbitol. In certain embodiments, the total amount of sugar alcohol (s), which are added to effectively aid in the dispersion or dissolution of the mouth rinse or other ingredients, should not exceed about 50% w/ of the total composition. Or, total amount of sugar alcohol should not exceed about 30% w/v of the total composition. Or, total amount of sugar alcohol should not exceed 25% w/v of the total composition. The sugar alcohol can be in an amount of from about 1.0% to about 24% w/v, or from about 1.5% to about 22% w/v, or from about 2.5% to about 20% w/v of the total composition.

In certain embodiments, a polyol solvent is added to the composition. The polyol solvent comprises a polyol or polyhydric alcohol selected from the group consisting of polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 0% to about 40% w/v, or from about 0.5% to about 20% w/v, or from about 1.0% to about 10% w/v of the composition.

In certain embodiments, the compositions of the present invention have a pH of about 11 or less. In some embodiments, the compositions have a pH of from about 3 to about 7, or from about 3.5 to about 6.5, or from about 3.5 to about 5.0.

As will be recognized by those of skill in the art, the pH of the composition may be adjusted or maintained using a buffer in an amount effective to provide the composition with a pH at or below 11. The composition can optionally comprise at least one pH modifying agents among those useful herein include acidifying agents to lower pH, basifying agents to raise pH, and buffering agents to maintain pH within a desired range. For example, one or more compounds selected from acidifying, basifying and buffering agents can be included to provide a pH of about 2 to about 7, or in various embodiments from about 3 to about 6, or from about 4 to about 5. Any orally acceptable pH modifying agent can be used including without limitation hydrochloric, carboxylic and sulfonic acids, acid salts (e.g., monosodium citrate, disodium citrate, monosodium malate, etc.), alkali metal hydroxides such as sodium hydroxide, borates, silicates, imidazole and mixtures thereof. One or more pH modifying agents are optionally present in a total amount effective to maintain the composition in an orally acceptable pH range. In certain embodiments, inorganic acids may be used as the buffer added to the composition.

In certain embodiments, organic acids may be used as the buffer added to the composition. Organic acids suitable for use in the compositions of the present invention include, but are not limited to, ascorbic acid, sorbic acid, citric acid, glycolic acid, lactic acid and acetic acid, benzoic acid, salicylic acid, phthalic acid, phenolsulphonic acid, and mixtures thereof, optionally, the organic acid is selected from the group consisting of benzoic acid, sorbic acid, citric acid and mixtures thereof, or optionally, the organic acid is benzoic acid.

Generally the amount of buffering compound is from about 0.001% to about 20.0% of the composition. In certain embodiment, the organic acid buffer is present in amounts of from about 0.001% to about 10% w/v of the composition, or from about 0.01% to about 1% of the composition.

In certain embodiments, additional conventional components may be added as in mouthwashes and mouth rinses of the prior art. Whereas some alcohol containing mouth rinses have a pH of about 7.0, reduction of the alcohol level may require the addition of acidic preservatives, such as sorbic acid or benzoic acid, which reduce pH levels. Buffer systems are then necessary to control the pH of the composition at optimal levels. This is generally accomplished through the addition of a weak acid and its salt or a weak base and its salt. In some embodiments, useful systems have been found to be sodium benzoate and benzoic acid in amounts of from 0.01% (or about 0.01% w/v) to 1.0% w/v (or about 1.0% w/v) of the composition, and sodium citrate and citric acid in amounts of from 0.001% (or about 0.001% w/v) to 1.0% w/v (or about 1.0% w/v) of the composition, phosphoric acid and sodium/potassium phosphate of amounts from 0.01% (or about 0.01%) to 1.0% (or about 1.0%) by weight of the composition. In certain embodiments, the buffers are incorporated in amounts that maintain the pH at levels of from 3.0 (or about 3.0) to 8.0 (or about 8.0), optionally from 3.5 (or about 3.5) to 6.5 (or about 6.5), optionally from 3.5 (or about 3.5) to 5.0 (or about 5.0).

Additional buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, sodium gluconate, sodium lactate, citric acid, and sodium citrate.

Sweeteners such as aspartame, sodium saccharin (saccharin), sucralose, stevia, acesulfame K and the like may be added for better taste in amounts of from about 0.0001% w/v to about 1.0% w/v. In certain preferred embodiments, the sweetener comprises sucralose.

In certain embodiments, the composition further comprises flavors or flavorants to modify or magnify the taste of the composition, or reduce or mask the sharp "bite" or "burn" of ingredients such as thymol. Suitable flavors include, but are not limited to, flavor oils such as oil of anise, anethole, benzyl alcohol, spearmint oil, citrus oils, vanillin and the like may be incorporated. Other flavors such as citrus oils, vanillin and the like may be incorporated to provide further taste variations. In these embodiments, the amount of flavor oil added to the composition can be from about 0.001% to about 5% w/v, or from about 0.01% to about 0.3% w/v of the total composition. The particular flavors or flavorants, and other taste improving ingredients, employed will vary depending upon the particular taste and feel desired. Those skilled in the art can select and customize these types of ingredients to provide the desired results.

In certain embodiments, acceptably approved food dyes may be used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from about 0.00001% w/v to about 0.0008% w/v, or from about 0.000035% w/v to about 0.0005% w/v of the composition.

Other conventional ingredients may be used in the liquid or mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from about 0.1% w/v to about 0.6% w/v, or about 0.5% w/v of the composition.

In some embodiments, antimicrobial preservatives may be added to the composition. Some antimicrobial preservatives which may be used include, but are not limited to cationic antibacterials, such as sodium benzoate, polyquaternium polycationic polymers (i.e polyquaternium-42: Poly[oxyethylene(dimethylimino)ethylene (dimethylimino)ethylene dichloride]), quaternary ammonium salts or quaternary ammonium compounds, parabens (i.e. parahydroxybenzoates or esters of parahydroxybenzoic acid), hydroxyacetophenone, 1,2-Hexanediol, Caprylyl Glycol, chlorhexidine, alexidine, hexetidine, benzalkonium chloride, domiphen bromide, cetylpyridinium chloride (CPC), tetradecylpyridinium chloride (TPC), N-tetradecyl-4-ethylpyridinium chloride (TDEPC), octenidine, bisbiguanides, zinc or stannous ion agents, grapefruit extract, and mixtures thereof. Other antibacterial and antimicrobial agents include, but are not limited to: 5-chloro-2-(2,4-dichlorophenoxy)-phenol, commonly referred to as triclosan; 8-hydroxyquinoline and its salts, copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, including magnesium monopotassium phthalate; sanguinarine; salicylanilide; iodine; sulfonamides; phenolics; delmopinol, octapinol, and other piperidino derivatives; niacin preparations; nystatin; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; pyrrolidone ethyl cocoyl arginate; lauroyl ethyl arginate monochlorohydrate; and mixtures of all of the above. In another embodiment, the composition comprises phenolic antimicrobial compounds and mixtures thereof. Antimicrobial components may be present from about 0.001% to about 20% by weight of the oral care composition. In another embodiment the antimicrobial agents generally comprise from about 0.1% to about 5% by weight of the oral care compositions of the present invention.

Other antibacterial agents may be basic amino acids and salts. Other embodiments may comprise arginine.

In certain embodiments, the compositions may include whitening agents, oxidizing agents, anti-inflammatories, chelating agents, abrasives, combinations thereof, and the like.

A whitening agent may be included as an active in the present compositions. The actives suitable for whitening are selected from the group consisting of alkali metal and alkaline earth metal peroxides, metal chlorites, polyphosphates, perborates inclusive of mono and tetrahydrates, perphosphates, percarbonates, peroxyacids, and persulfates, such as ammonium, potassium, sodium and lithium persulfates, and combinations thereof. Suitable peroxide compounds include hydrogen peroxide, urea peroxide, calcium peroxide, carbamide peroxide, magnesium peroxide, zinc peroxide, strontium peroxide and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine, respectively, that the molecule is capable of providing to bleach the stain. In one embodiment the whitening agents may be present at levels from about 0.01% to about 40%, in another embodiment from about 0.1% to about 20%, in another embodiment form about 0.5% to about 10%, and in another embodiment from about 4% to about 7%, by weight of the oral care composition.

The compositions of the invention may contain an oxidizing agent, such as a peroxide source. A peroxide source may comprise hydrogen peroxide, calcium peroxide, carbamide peroxide, or mixtures thereof. In some embodiments, the peroxide source is hydrogen peroxide. Other peroxide actives can include those that produce hydrogen peroxide when mixed with water, such as percarbonates, e.g., sodium percarbonates. In certain embodiments, the peroxide source may be in the same phase as a stannous ion source. In some embodiments, the composition comprises from about 0.01% to about 20% of a peroxide source, in other embodiments from about 0.1% to about 5%, in certain embodiments from about 0.2% to about 3%, and in another embodiment from about 0.3% to about 2.0% of a peroxide source, by weight of the oral composition. The peroxide source may be provided as free ions, salts, complexed, or encapsulated. It is desirable that the peroxide in the composition is stable. The peroxide may provide a reduction in staining, as measured by the Cycling Stain Test, or other relevant methods.

Anti-inflammatory agents can also be present in the compositions of the present invention. Such agents may include, but are not limited to, non-steroidal anti-inflammatory (NSAID) agents oxicams, salicylates, propionic acids, acetic acids and fenamates. Such NSAIDs include but are not limited to ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as ketorolac are claimed in U.S. Pat. No. 5,626,838. Disclosed therein are methods of preventing and/or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

The present compositions may optionally contain chelating agents, also called chelants or sequestrants, many of which also have anticalculus activity or tooth substantive activity. Use of chelating agents in oral care products is advantageous for their ability to complex calcium such as found in the cell walls of bacteria. Chelating agents can also disrupt plaque by removing calcium from the calcium bridges which help hold this biomass intact. Chelating agents also have the ability to complex with metallic ions and thus aid in preventing their adverse effects on the stability or appearance of products. Chelation of ions, such as iron or copper, helps retard oxidative deterioration of finished products. In addition, chelants can in principle remove stains by binding to teeth surfaces thereby displacing color bodies or chromagens. The retention of these chelants can also prevent stains from accruing due to disruption of binding sites of color bodies on tooth surfaces. Therefore, chelants can aid in helping to mitigate stain and improve cleaning. A chelant may help to improve the cleaning as fused silica and abrasives clean in a mechanical mechanism while the chelant may help to provide chemical cleaning Because the fused silica is a good mechanical cleaner, there may be more stain removed so a chelant may be desired to hold, suspend, or complex with the stain so it is not able to restain the tooth surface. Additionally, the chelant may coat the surface of the tooth to help prevent new stain. Chelants may be desired to be added to formulations containing cationic antibacterial agents. It may be desired to add chelants to stannous containing formulations. The chelant is able to help stabilize the stannous and keep a higher amount of the stannous bioavailable. The chelant may be used in stannous formulations which have a pH above about 4.0. In some formulations, the stannous may be stable without the need for a chelant as the stannous is more stable with fused silica as compared to precipitated silica.

Suitable chelating agents include soluble phosphate compounds, such as phytates and linear polyphosphates having two or more phosphate groups, including tripolyphosphate, tetrapolyphosphate and hexametaphosphate, among others. Preferred polyphosphates are those having the number of phosphate groups n averaging from about 6 to about 21, such as those commercially known as Sodaphos (n≈6), Hexaphos (n≈13), and Glass H (n≈21). Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds. The amount of chelating agent in the compositions will depend on the chelating agent used and typically will be from at least about 0.1% to about 20%, preferably from about 0.5% to about 10% and more preferably from about 1.0% to about 7%.

Still other phosphate compounds that are useful herein for their ability to bind, solubilize and transport calcium are the surface active organophosphate compounds described above useful as tooth substantive agents including organic phosphate mono-, di- or triesters.

Other suitable agents with chelating properties for use in controlling plaque, calculus and stain include polyphosphonates described in U.S. Pat. No. 3,678,154 to Widder et al., U.S. Pat. No. 5,338,537 to White, Jr., and U.S. Pat. No. 5,451,401 to Zerby et al.; carbonyl diphosphonates in U.S. Pat. No. 3,737,533 to Francis; acrylic acid polymer or copolymer in U.S. Pat. No. 4,847,070, Jul. 11, 1989 to Pyrz et al. and in U.S. Pat. No. 4,661,341, Apr. 28, 1987 to Benedict et al.; sodium alginate in U.S. Pat. No. 4,775,525, issued Oct. 4, 1988, to Pera; polyvinyl pyrrolidone in GB 741,315, WO 99/12517 and U.S. Pat. No. 5,538,714 to Pink et al.; and copolymers of vinyl pyrrolidone with carboxylates in U.S. Pat. No. 5,670,138 to Venema et al. and in JP Publication No. 2000-063250 to Lion Corporation.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez® AN 139 (M.W. 500,000), AN 119 (M.W. 250,000) and S-97 Pharmaceutical Grade (M.W. 70,000), of GAF Chemicals Corporation. Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2. Other suitable chelants include polycarboxylic acids and salts thereof described in U.S. Pat. No. 5,015,467 to Smitherman U.S. Pat. Nos. 5,849,271 and 5,622,689 both to Lukacovic; such as tartaric acid, citric acid, gluconic acid, malic acid; succinic acid, disuccinic acid and salts thereof, such as sodium or potassium gluconate and citrate; citric acid/alkali metal citrate combination; disodium tartrate; dipotassium tartrate; sodium potassium tartrate; sodium hydrogen tartrate; potassium hydrogen tartrate; acid or salt form of sodium tartrate monosuccinate, potassium tartrate disuccinate, and mixtures thereof. In some embodiments, there may be mixtures or combinations of chelating agents.

Suitable abrasives for use in the present invention may include, but are not limited to: perlite, silica such as sand or quartz, ground glass, silicon carbide, ilmenite ($FeTiO_3$), zircon oxide, zircon silicate, topaz, $TiO_2$, precipitated lime, chalk, flour of pumice, zeolites, talcum, kaolin, kieselguhr, aluminium oxide, silicates, zinc orthophosphate, sodium bicarbonate (baking soda), plastic particles, alumina, hydrated alumina, calcium carbonate, calcium pyrophosphate, and mixtures thereof. The silica abrasive may be a natural amorphous silica including diatomaceous earth; or a synthetic amorphous silica such as a precipitated silica; or a silica gel, such as a silica xerogel; or mixtures thereof.

Generally, an amount of abrasive suitable for use in the composition of the invention will be empirically determined to provide an acceptable level of cleaning and polishing, in accordance with the techniques well known in the art. In one embodiment, a composition of the present invention includes an abrasive. In one embodiment, a composition includes a silica abrasive. In one embodiment, a silica abrasive is present in an amount of from 0.001 wt. % to 30 wt. %. In one embodiment, a silica abrasive is present in an amount of from 1 wt. % to 15 wt. %. In one embodiment, a silica abrasive is present in an amount of from 4 wt. % to 10 wt. %

Other useful oral care actives and/or inactive ingredients and further examples thereof can be found in U.S. Pat. No. 6,682,722 to Majeti et al. and U.S. Pat. No. 6,121,315 to Nair et al., each of which are herein incorporated by reference in its entirety.

The compositions of the present invention may be made according to any of a variety of methods disclosed herein and known in the art. In general, the described compositions may be prepared by combining the desired components in a suitable container and mixing them under ambient conditions in any conventional mixing means well known in the art, such as a mechanically stirred propeller, paddle, and the like.

The compounds and compositions of the present invention may be used in a variety of methods of treating a mammalian body, in particular for disrupting a biofilm on a surface of the oral cavity. According to certain embodiments, the present invention comprises disrupting biofilm on a surface by contacting the surface comprising biofilm with a composition of the present invention. In certain embodiments, the present invention comprises removing biofilm from a surface by contacting the surface comprising biofilm with a composition of the present invention. In certain embodiments, the present invention comprises reducing bacterial attachment to a surface by contacting the surface with a composition of the present invention.

Any suitable surface of the oral cavity may be contacting in accord with the methods of the present invention including one or more surfaces selected from the group consisting of surfaces of one or more teeth, surfaces of the gums, combinations of two or more thereof, and the like.

In each of the above methods, the composition of the claimed method may be introduced to the surface to be contacted via any of a variety of methods. In certain embodiments, the composition is introduced into the oral cavity and applied to the surface by a user as a mouthwash or mouth rinse. In certain embodiments, the composition is introduced to the oral cavity and applied to the surface as a toothpaste on an article for cleaning the teeth, e.g. a toothbrush. The compositions of the present invention may be further introduced via the mouth and applied to the surface as a gum, lozenge, dissolvable strip, or the like.

Furthermore, the contacting step of the methods of the present invention may comprise contacting the surface with the composition for any suitable amount of time. In certain embodiments, the contacting step comprises contacting the surface for less than thirty seconds. In certain embodiments, the contacting step comprises contacting the surface with the composition for thirty seconds or more, for example, for about thirty seconds, for about 40 seconds, for about one minute, or for greater than one minute.

EXAMPLES

Example 1

Biofilm Prevention Performance of Compounds

Formulations A1-J1 as shown in Table 1 were made by dissolving one of nine compounds: transcis-aconitic acid, succinic acid, adenosine, quinic acid, inosine, shikimic acid, uridine, oxalic acid, or epicatechin, in an aqueous solution containing ethanol and a benzoic acid buffer. Each of the nine formulations were tested in a biofilm prevention assay as described below.

The formulations were used to treat pellicle-coated hydroxyapatite peg lids by immersing the lids in the formulations as treatment solutions. The peg lids were then removed from the treatment solutions and inoculated overnight with human whole saliva, in order to generate a mixed species saliva-derived biofilm. The amount of biofilm grown on each peg lid was quantified by measuring ATP using a bioluminescence reaction, and compared to the amount of biofilm grown on a peg lid exposed to the benzoic acid/ethanol solution negative control (sample J). The results are reported as log RLU, with a lower value corresponding to less biofilm. The resulting Log RLUs are reported in Table 1.

TABLE 1

| | Formulations of nine components. | | | | | | | | |
|---|---|---|---|---|---|---|---|---|---|
| Raw Material (w/w %) | A1 | B1 | C1 | D1 | E1 | F1 | G1 | H1 | I1 | J1 |
| cis-Aconitic acid | 0.5 | — | — | — | — | — | — | — | — | — |
| Succinic acid | — | 0.5 | — | — | — | — | — | — | — | — |
| Adenosine | — | — | 0.5 | — | — | — | — | — | — | — |
| Quinic acid | — | — | — | 0.5 | — | — | — | — | — | — |
| Inosine | — | — | — | — | 0.5 | — | — | — | — | — |
| Shikimic acid | — | — | — | — | — | 0.5 | — | — | — | — |
| Uridine | — | — | — | — | — | — | 0.5 | — | — | — |
| Oxalic acid | — | — | — | — | — | — | — | 0.5 | — | — |
| Epicatechin | — | — | — | — | — | — | — | — | 0.5 | — |

TABLE 1-continued

Formulations of nine components.

| Raw Material (w/w %) | A1 | B1 | C1 | D1 | E1 | F1 | G1 | H1 | I1 | J1 |
|---|---|---|---|---|---|---|---|---|---|---|
| Benzoic acid | 0.15 | 0.15 | 0.15 | 0.15 | 0.15 | 0.15 | 0.15 | 0.15 | 0.15 | 0.15 |
| Ethanol | 17.94 | 17.94 | 17.94 | 17.94 | 17.94 | 17.94 | 17.94 | 17.94 | 17.94 | 17.94 |
| Water | 81.4 | 81.4 | 81.4 | 81.4 | 81.4 | 81.4 | 81.4 | 81.4 | 81.4 | 81.4 |
| TOTAL | 100.0 | 100.0 | 100.0 | 100.0 | 100.0 | 100.0 | 100.0 | 100.0 | 100.0 | 100.0 |
| log RLU | 5.90 | 5.94 | 6.17 | 6.17 | 6.17 | 6.20 | 6.23 | 6.37 | 6.68 | 6.30 |
| log SD | 0.11 | 0.11 | 0.14 | 0.10 | 0.14 | 0.05 | 0.13 | 0.07 | 0.08 | 0.08 |

Example 2

Exploration of Different Ratios and Concentration Ranges for Succinic Acid/Trans-Aconitic Acid Succinic acid and trans-aconitic acid were formulated into full mouth rinse formulations and their concentrations and ratios were systematically varied. The amounts and materials of each formulation is shown on Tables 2 through 5. Formulations containing succinic acid, trans-aconitic acid, and blends of both succinic acid and trans-aconitic acid were made. The total concentration of succinic acid plus trans-aconitic acid used in the formulations shown on Tables 3 through 6 are 10.5 mM, 21 mM, 42 mM, and 63 mM, i.e. between 0.12% w/w and 1.1% w/w, respectively. These formulations were prepared by dissolving water soluble components, including succinic acid, trans-aconitic acid, Poloxamer 407, sodium lauryl sulfate, sodium benzoate, saccharin, sucralose, sorbitol, and FD&C Green#3, in water. Separately, all non-water soluble components, including menthol, thymol, eucalyptol, methyl salicylate, flavor, and benzoic acid, were dissolved in propylene glycol. The propylene glycol solution was then added to the aqueous solution and mixed.

TABLE 2

Formulations to find synergies of succinic acid (SA) and t-aconitic acid (tAA) mixtures. Total concentration of SA and tAA was 10.5 mM, 0.12-0.18% by weight or 0.15% +/− 0.03%

| Raw material (w/w %) | A10.5 | B10.5 | C10.5 | D10.5 | E10.5 | F10.5 | G10.5 | H10.5 | I10.5 |
|---|---|---|---|---|---|---|---|---|---|
| Succinic Acid | 0.071 | 0.088 | 0.11 | 0.11 | 0.12 | 0.12 | 0.12 | 0.12 | — |
| Aconitic Acid | 0.078 | 0.052 | 0.026 | 0.020 | 0.013 | 0.0087 | 0.0044 | — | 0.18 |
| Menthol | 0.019 | 0.019 | 0.019 | 0.019 | 0.019 | 0.019 | 0.019 | 0.019 | 0.019 |
| Thymol | 0.031 | 0.031 | 0.031 | 0.031 | 0.031 | 0.031 | 0.031 | 0.031 | 0.031 |
| Methyl Salicylate | 0.032 | 0.032 | 0.032 | 0.032 | 0.032 | 0.032 | 0.032 | 0.032 | 0.032 |
| Eucalyptol | 0.045 | 0.045 | 0.045 | 0.045 | 0.045 | 0.045 | 0.045 | 0.045 | 0.045 |
| Poloxamer 407 | 0.10 | 0.10 | 0.10 | 0.10 | 0.10 | 0.10 | 0.10 | 0.10 | 0.10 |
| Sodium Lauryl Sulfate | 0.10 | 0.10 | 0.10 | 0.10 | 0.10 | 0.10 | 0.10 | 0.10 | 0.10 |
| Benzoic Acid | 0.05 | 0.05 | 0.05 | 0.05 | 0.05 | 0.05 | 0.05 | 0.05 | 0.05 |
| Sodium Benzoate | 0.11 | 0.11 | 0.11 | 0.11 | 0.11 | 0.11 | 0.11 | 0.11 | 0.11 |
| Saccharin | 0.061 | 0.061 | 0.061 | 0.061 | 0.061 | 0.061 | 0.061 | 0.061 | 0.061 |
| Sucralose | 0.010 | 0.010 | 0.010 | 0.010 | 0.010 | 0.010 | 0.010 | 0.010 | 0.010 |
| Propylene Glycol | 7.0 | 7.0 | 7.0 | 7.0 | 7.0 | 7.0 | 7.0 | 7.0 | 7.0 |
| Sorbitol | 10.0 | 10.0 | 10.0 | 10.0 | 10.0 | 10.0 | 10.0 | 10.0 | 10.0 |
| FD&C Green #3 | 0.000037 | 0.000037 | 0.000037 | 0.000037 | 0.000037 | 0.000037 | 0.000037 | 0.000037 | 0.000037 |
| Flavor | 0.017 | 0.017 | 0.017 | 0.017 | 0.017 | 0.017 | 0.017 | 0.017 | 0.017 |
| Water | 82.3 | 82.3 | 82.3 | 82.3 | 82.3 | 82.3 | 82.3 | 82.2 | 82.4 |
| TOTAL | 100.0 | 100.0 | 100.0 | 100.0 | 100.0 | 100.0 | 100.0 | 100.0 | 100.0 |
| [SA]/[tAA] ratio | 0.9:1 | 1.7:1 | 4.2:1 | 5.5:1 | 9.2:1 | 13.8:1 | 27.3:1 | — | — |

TABLE 3

Formulations to find synergies of succinic acid (SA) and t-aconitic acid (tAA) mixtures. Total concentration of SA and tAA was 21 mM, 0.25%-0.37% w/w

| Raw material | A21 | B21 | C21 | D21 | E21 | F21 |
|---|---|---|---|---|---|---|
| Succinic Acid | 0.035 | 0.071 | 0.11 | 0.14 | 0.18 | 0.21 |
| trans-AconiticAcid | 0.31 | 0.26 | 0.21 | 0.16 | 0.10 | 0.052 |
| Menthol | 0.019 | 0.019 | 0.019 | 0.019 | 0.019 | 0.019 |
| Thymol | 0.031 | 0.031 | 0.031 | 0.031 | 0.031 | 0.031 |
| Methyl Salicylate | 0.032 | 0.032 | 0.032 | 0.032 | 0.032 | 0.032 |
| Eucalyptol | 0.045 | 0.045 | 0.045 | 0.045 | 0.045 | 0.045 |
| Poloxamer 407 | 0.10 | 0.10 | 0.10 | 0.10 | 0.10 | 0.10 |
| Sodium Lauryl Sulfate | 0.10 | 0.10 | 0.10 | 0.10 | 0.10 | 0.10 |

TABLE 3-continued

Formulations to find synergies of succinic acid (SA) and t-aconitic acid (tAA) mixtures. Total concentration of SA and tAA was 21 mM, 0.25%-0.37% w/w

| | | | | | | |
|---|---|---|---|---|---|---|
| Benzoic Acid | 0.05 | 0.05 | 0.05 | 0.05 | 0.05 | 0.05 |
| Sodium Benzoate | 0.11 | 0.11 | 0.11 | 0.11 | 0.11 | 0.11 |
| Saccharin | 0.061 | 0.061 | 0.061 | 0.061 | 0.061 | 0.061 |
| Sucralose | 0.010 | 0.010 | 0.010 | 0.010 | 0.010 | 0.010 |
| Propylene Glycol | 7.0 | 7.0 | 7.0 | 7.0 | 7.0 | 7.0 |
| Sorbitol | 10.0 | 10.0 | 10.0 | 10.0 | 10.0 | 10.0 |
| FD&C Green #3 | 0.000037 | 0.000037 | 0.000037 | 0.000037 | 0.000037 | 0.000037 |
| Flavor | 0.017 | 0.017 | 0.017 | 0.017 | 0.017 | 0.017 |
| Water | 82.1 | 82.1 | 82.1 | 82.1 | 82.1 | 82.2 |
| TOTAL | 100.0 | 100.0 | 100.0 | 100.0 | 100.0 | 100.0 |
| [SA]/[tAA] | 0.1:1 | 0.3:1 | 0.5:1 | 0.9:1 | 1.8:1 | 4:1 |

| Raw material | G21 | H21 | I21 | J21 | K21 | L21 |
|---|---|---|---|---|---|---|
| Succinic Acid | 0.22 | 0.23 | 0.24 | 0.24 | 0.25 | — |
| trans-Aconitic Acid | 0.039 | 0.026 | 0.017 | 0.0087 | — | 0.37 |
| Menthol | 0.019 | 0.019 | 0.019 | 0.019 | 0.019 | 0.019 |
| Thymol | 0.031 | 0.031 | 0.031 | 0.031 | 0.031 | 0.031 |
| Methyl Salicylate | 0.032 | 0.032 | 0.032 | 0.032 | 0.032 | 0.032 |
| Eucalyptol | 0.045 | 0.045 | 0.045 | 0.045 | 0.045 | 0.045 |
| Poloxamer 407 | 0.10 | 0.10 | 0.10 | 0.10 | 0.10 | 0.10 |
| Sodium Lauryl Sulfate | 0.10 | 0.10 | 0.10 | 0.10 | 0.10 | 0.10 |
| Benzoic Acid | 0.05 | 0.05 | 0.05 | 0.05 | 0.05 | 0.05 |
| Sodium Benzoate | 0.11 | 0.11 | 0.11 | 0.11 | 0.11 | 0.11 |
| Saccharin | 0.061 | 0.061 | 0.061 | 0.061 | 0.061 | 0.061 |
| Sucralose | 0.010 | 0.010 | 0.010 | 0.010 | 0.010 | 0.010 |
| Propylene Glycol | 7.0 | 7.0 | 7.0 | 7.0 | 7.0 | 7.0 |
| Sorbitol | 10.0 | 10.0 | 10.0 | 10.0 | 10.0 | 10.0 |
| FD&C Green #3 | 0.000037 | 0.000037 | 0.000037 | 0.000037 | 0.000037 | 0.000037 |
| Flavor | 0.017 | 0.017 | 0.017 | 0.017 | 0.017 | 0.017 |
| Water | 82.2 | 82.2 | 82.2 | 82.2 | 82.2 | 82.0 |
| TOTAL | 100.0 | 100.0 | 100.0 | 100.0 | 100.0 | 100.0 |
| [SA]/[tAA] | 5.6:1 | 8.8:1 | 14.1:1 | 27.6:1 | — | — |

TABLE 4

Formulations to find synergies of succinic acid (SA) and t-aconitic acid (tAA) mixtures. Total concentration of SA and tAA was 42 mM, 0.50-0.73% w/w

| Raw material | A42 | B42 | C42 | D42 | E42 | F42 | G42 | H42 | I42 |
|---|---|---|---|---|---|---|---|---|---|
| Succinic Acid | 0.28 | 0.35 | 0.42 | 0.44 | 0.46 | 0.47 | 0.48 | 0.5 | — |
| trans-aconitic Acid | 0.31 | 0.21 | 0.10 | 0.078 | 0.052 | 0.035 | 0.017 | — | 0.73 |
| Menthol | 0.019 | 0.019 | 0.019 | 0.019 | 0.019 | 0.019 | 0.019 | 0.019 | 0.019 |
| Thymol | 0.031 | 0.031 | 0.031 | 0.031 | 0.031 | 0.031 | 0.031 | 0.031 | 0.031 |
| Methyl Salicylate | 0.032 | 0.032 | 0.032 | 0.032 | 0.032 | 0.032 | 0.032 | 0.032 | 0.032 |
| Eucalyptol | 0.045 | 0.045 | 0.045 | 0.045 | 0.045 | 0.045 | 0.045 | 0.045 | 0.045 |
| Poloxamer 407 | 0.10 | 0.10 | 0.10 | 0.10 | 0.10 | 0.10 | 0.10 | 0.10 | 0.10 |
| Sodium Lauryl Sulfate | 0.10 | 0.10 | 0.10 | 0.10 | 0.10 | 0.10 | 0.10 | 0.10 | 0.10 |
| Benzoic Acid | 0.05 | 0.05 | 0.05 | 0.05 | 0.05 | 0.05 | 0.05 | 0.05 | 0.05 |
| Sodium Benzoate | 0.11 | 0.11 | 0.11 | 0.11 | 0.11 | 0.11 | 0.11 | 0.11 | 0.11 |
| Saccharin | 0.061 | 0.061 | 0.061 | 0.061 | 0.061 | 0.061 | 0.061 | 0.061 | 0.061 |
| Sucralose | 0.010 | 0.010 | 0.010 | 0.010 | 0.010 | 0.010 | 0.010 | 0.010 | 0.010 |
| Propylene Glycol | 7.0 | 7.0 | 7.0 | 7.0 | 7.0 | 7.0 | 7.0 | 7.0 | 7.0 |
| Sorbitol | 10.0 | 10.0 | 10.0 | 10.0 | 10.0 | 10.0 | 10.0 | 10.0 | 10.0 |
| FD&C Green #3 | 0.000037 | 0.000037 | 0.000037 | 0.000037 | 0.000037 | 0.000037 | 0.000037 | 0.000037 | 0.000037 |
| Flavor | 0.017 | 0.017 | 0.017 | 0.017 | 0.017 | 0.017 | 0.017 | 0.017 | 0.017 |
| Water | 81.8 | 81.9 | 81.9 | 81.9 | 81.9 | 81.9 | 81.9 | 81.9 | 81.7 |
| TOTAL | 100.0 | 100.0 | 100.0 | 100.0 | 100.0 | 100.0 | 100.0 | 100.0 | 100.0 |
| [SA]/[tAA] | 0.9:1 | 1.7:1 | 4.2:1 | 5.6:1 | 8.8:1 | 13.4:1 | 28.2:1 | — | — |

TABLE 5

Formulations to find synergies of succinic acid (SA) and t-aconitic acid (tAA) mixtures.
Total concentration of SA and tAA was 63 mM, 0.74-1.10% w/w

| Raw material | A63 | B63 | C63 | D63 | E63 | F63 | G63 | H63 | I63 |
|---|---|---|---|---|---|---|---|---|---|
| Succinic Acid | 0.42 | 0.53 | 0.64 | 0.66 | 0.69 | 0.71 | 0.73 | 0.74 | — |
| Aconitic Acid | 0.47 | 0.31 | 0.16 | 0.12 | 0.078 | 0.052 | 0.026 | — | 1.10 |
| Menthol | 0.019 | 0.019 | 0.019 | 0.019 | 0.019 | 0.019 | 0.019 | 0.019 | 0.019 |
| Thymol | 0.031 | 0.031 | 0.031 | 0.031 | 0.031 | 0.031 | 0.031 | 0.031 | 0.031 |
| Methyl Salicylate | 0.032 | 0.032 | 0.032 | 0.032 | 0.032 | 0.032 | 0.032 | 0.032 | 0.032 |
| Eucalyptol | 0.045 | 0.045 | 0.045 | 0.045 | 0.045 | 0.045 | 0.045 | 0.045 | 0.045 |
| Poloxamer 407 | 0.10 | 0.10 | 0.10 | 0.10 | 0.10 | 0.10 | 0.10 | 0.10 | 0.10 |
| Sodium Lauryl Sulfate | 0.10 | 0.10 | 0.10 | 0.10 | 0.10 | 0.10 | 0.10 | 0.10 | 0.10 |
| Benzoic Acid | 0.05 | 0.05 | 0.05 | 0.05 | 0.05 | 0.05 | 0.05 | 0.05 | 0.05 |
| Sodium Benzoate | 0.11 | 0.11 | 0.11 | 0.11 | 0.11 | 0.11 | 0.11 | 0.11 | 0.11 |
| Saccharin | 0.061 | 0.061 | 0.061 | 0.061 | 0.061 | 0.061 | 0.061 | 0.061 | 0.061 |
| Sucralose | 0.010 | 0.010 | 0.010 | 0.010 | 0.010 | 0.010 | 0.010 | 0.010 | 0.010 |
| Propylene Glycol | 7.0 | 7.0 | 7.0 | 7.0 | 7.0 | 7.0 | 7.0 | 7.0 | 7.0 |
| Sorbitol | 10.0 | 10.0 | 10.0 | 10.0 | 10.0 | 10.0 | 10.0 | 10.0 | 10.0 |
| FD&C Green #3 | 0.000037 | 0.000037 | 0.000037 | 0.000037 | 0.000037 | 0.000037 | 0.000037 | 0.000037 | 0.000037 |
| Flavor | 0.017 | 0.017 | 0.017 | 0.017 | 0.017 | 0.017 | 0.017 | 0.017 | 0.017 |
| Water | 81.5 | 81.6 | 81.6 | 81.6 | 81.6 | 81.7 | 81.7 | 81.7 | 81.3 |
| TOTAL | 100.0 | 100.0 | 100.0 | 100.0 | 100.0 | 100.0 | 100.0 | 100.0 | 100.0 |
| [SA]/[tAA] | 0.9:1 | 1.7:1 | 4.0:1 | 5.5:1 | 8.8:1 | 13.7:1 | 28.1:1 | — | — |

Two methods were used to test the effectiveness of the formulations. The first was a "Multi-Treatment Static Biofilm with Pretreatment Assay Method", while the second was a "Prevention Assay Method". The test methods are described below.

Multi Treatment Static Biofilm with Pretreatment Assay Method

The formulations were prepared as described above using conventional mixing technology. The pH of the formulations were all about pH 4.2. A polystyrene peg plate (96 pegs, N=8 per group) were exposed to saliva for thirty minutes to form a pellicle on each peg at a temperature of 35° C. Then, for each formulation, eight pegs (N=8) were pre-treated for ten minutes with the formulation using an orbital shaker set to 500 RPM at room temperature. As a negative control, eight pegs (N=8) were pre-treated for ten minutes with sterile water. Next, a 24-hour salivary biofilm was grown on these polystyrene peg plates at a temperature of 35° C. The pegs were then re-treated (N=8) for thirty seconds with the same formulation used for pre-treatment using an orbital shaker set to 500 RPM at room temperature. The re-treatments were applied twice daily for two days, a total of six treatments including the pre-treatment.

After all treatments were complete, the biofilm from each peg was neutralized and rinsed. The biofilm was harvested via sonication using a Q-Sonica Q700 Ultrasonic Liquid Processor with 431MP4-00 microplate horn Damper and 0.5:1 reverse gain booster (Q-Sonica, Newtown, Conn.). Using a Celsis Rapid Detection RapiScreen kit (Celsis International PLC, Chicago, Ill.), the bacteria were lysed with Celsis Luminex and then the adenosine triphosphate (ATP) from the lysed bacteria was measured using the bioluminescence marker Celcis Luminate and a Centro LB 960 Microplate Luminometer supplied by Berthold Technologies (Wildbad, Germany). Data were reported in log RLU (relative light units) where decreasing log RLUs indicated fewer viable bacteria remained on the biofilm substrate.

Prevention Assay Method

The formulations were prepared as described above using conventional mixing technology. The pH of the formulations were all about pH 4.2. A hydroxyapatite-coated polystyrene peg plate (96 pegs, N=8 per group) was exposed to saliva for one minute to form a pellicle at a temperature of 35 C. Then, for each formulation, eight pegs (N=8) were pre-treated for ten minutes with the formulation using an orbital shaker set to 500 RPM at room temperature. As a negative control, eight pegs (N=8) were pre-treated for ten minutes with sterile water. Next, a 16-hour salivary biofilm was grown on these polystyrene peg plates at a temperature of 35 C.

After all treatments were complete, the biofilm from each peg was neutralized and rinsed. The biofilm was harvested via sonication using a Q-Sonica Q700 Ultrasonic Liquid Processor with 431MP4-00 microplate horn Damper and 0.5:1 reverse gain booster (Q-Sonica, Newtown, Conn.). Using a Celsis Rapid Detection RapiScreen kit (Celsis International PLC, Chicago, Ill.), the bacteria were lysed with Celsis Luminex and then the adenosine triphosphate (ATP) from the lysed bacteria was measured using the bioluminescence marker Celcis Luminate and a Centro LB 960 Microplate Luminometer supplied by Berthold Technologies (Wildbad, Germany). Data were reported in log RLU (relative light units) where decreasing log RLUs indicated fewer viable bacteria remained on the biofilm substrate.

The results of the "Multi-Treatment Static Biofilm with Pretreatment Assay Method", and the "Prevention Assay Method" for each of the formulations are summarized in Table 6.

Figure 2:
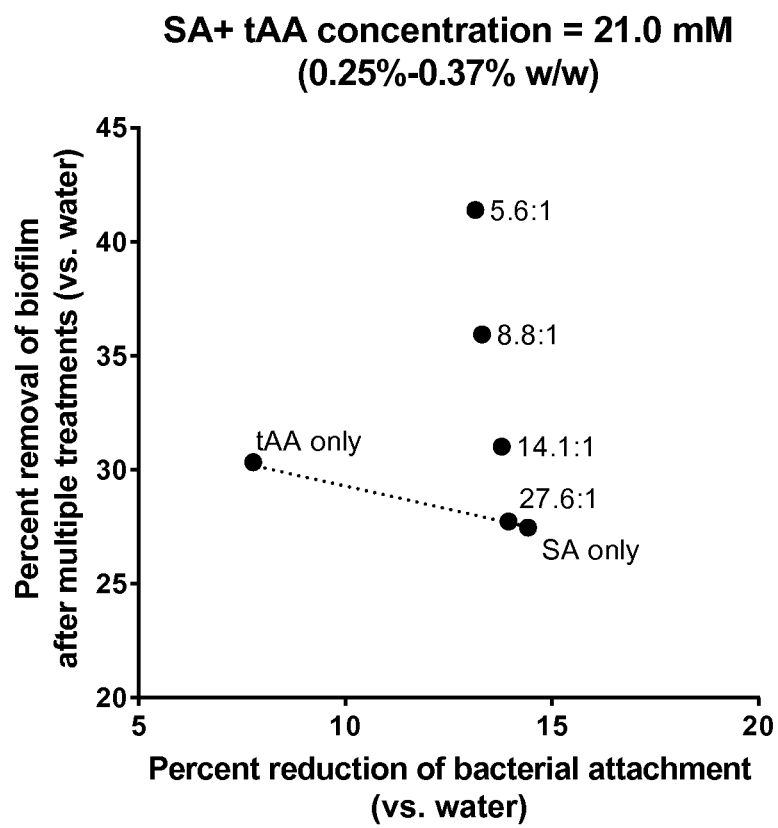
FIG. 2 is a plot of the percent removal of biofilm after multiple treatments (vs. water) versus percent reduction of bacterial attachment (vs. water) for formulations containing succinic acid (SA) and aconitic acid (AA) in varying ratios (different from those in FIG. 1) at a total concentration of 21 mM (0.25-0.37% w/w, depending on the ratio of SA to AA, see table 7).

FIGS. 1 and 2 are plots of the percent removal of biofilm after multiple treatments (vs. water) versus percent reduction of bacterial attachment (vs. water) for formulations A21-L21 containing succinic acid (SA) and trans-aconitic acid (tAA) shown in Table 3 above. The dotted lines on the figures are the straight line expected results of the blends of SA and tAA. The figures show that when succinic acid and trans-aconitic acid are combined in ratios between 0.9:1 and 14.1:1 (Succinic acid:trans-aconitic acid), the results deviate surprisingly from the expected results.

Table 6 shows the same surprising results when examining the distance from the expected results for blends of succinic acid and trans-aconitic acid for other concentrations of the combined acid materials in the Table.

TABLE 6

Summarized results for Multi-Treatment and Prevention tests for formulations containing succinic acid (SA) and trans-aconitic acid (tAA).

| | Formula | SA + tAA wt % | [SA]/[tAA] | Biofilm removal (log RLU) | Biofilm removal (% reduced over water control) | Reduction of baterial attachment (log RLU) | Reduction of bacterial attachment (% reduced over water control) | Predicted additive reduction in % biofilm reduction (prevention + multi-treatment)* compared to water control | Actual reduction of total biofilm (prevention + multi-treatment)** compared to water control |
|---|---|---|---|---|---|---|---|---|---|
| Experiment 1 | I10.5 | 0.18 | 0:1 | 4.66 | 35.72 | 6.00 | 6.40 | 42.12 | 42.12 |
| | A10.5 | 0.15 | 0.9:1 | 4.53 | 37.52 | 5.86 | 8.58 | 43.11 | 46.1 |
| | B10.5 | 0.14 | 1.7:1 | 4.42 | 39.03 | 5.79 | 9.67 | 43.44 | 48.7 |
| | C10.5 | 0.14 | 4.2:1 | 4.46 | 38.48 | 5.61 | 12.48 | 43.82 | 50.96 |
| | H10.5 | 0.12 | 1:0 | 5.13 | 29.24 | 5.45 | 14.98 | 44.22 | 44.22 |
| | water | 0.00 | — | 7.25 | 0.00 | 6.41 | 0.00 | 0.00 | 0.00 |
| Experiment 2 | I10.5 | 0.18 | 0:1 | 5.13 | 29.92 | 5.81 | 9.36 | 39.28 | 39.28 |
| | D10.5 | 0.13 | 5.5:1 | 4.48 | 38.80 | 5.63 | 12.17 | 41.75 | 50.97 |
| | E10.5 | 0.13 | 9.2:1 | 4.83 | 34.02 | 5.47 | 14.66 | 41.95 | 48.68 |
| | F10.5 | 0.13 | 13.8:1 | 5.06 | 30.87 | 5.5 | 14.20 | 42.04 | 45.07 |
| | G10.5 | 0.12 | 27.3:1 | 5.44 | 25.68 | 5.48 | 14.51 | 42.14 | 40.19 |
| | H10.5 | 0.12 | 1:0 | 5.37 | 26.64 | 5.41 | 15.60 | 42.24 | 42.24 |
| | water | 0.00 | — | 7.32 | 0.00 | 6.41 | 0.00 | 0.00 | 0 |
| Experiment 3 | L21 | 0.37 | 0:1 | 4.61 | 39.10 | 5.67 | 14.22 | 53.32 | 53.32 |
| | A21 | 0.35 | 0.1:1 | 4.6 | 39.23 | 5.65 | 14.52 | 53.32 | 53.75 |
| | B21 | 0.33 | 0.3:1 | 4.92 | 35.01 | 5.58 | 15.58 | 53.32 | 50.59 |
| | C21 | 0.32 | 0.5:1 | 4.81 | 36.46 | 5.5 | 16.79 | 53.31 | 53.25 |
| | D21 | 0.30 | 0.9:1 | 4.42 | 41.61 | 5.29 | 19.97 | 53.32 | 61.58 |
| | E21 | 0.28 | 1.8:1 | 4.14 | 45.31 | 5.26 | 20.42 | 53.31 | 65.73 |
| | F21 | 0.26 | 4.0:1 | 4.65 | 38.57 | 5.2 | 21.33 | 53.30 | 59.9 |
| | K21 | 0.25 | 1:0 | 5.23 | 30.91 | 5.13 | 22.39 | 53.30 | 53.3 |
| | water | 0.00 | — | 7.57 | 0.00 | 6.61 | 0.00 | 0.00 | 0 |
| Experiment 4 | L21 | 0.37 | 0:1 | 5.1 | 30.33 | 5.82 | 7.77 | 38.10 | 38.1 |
| | G21 | 0.26 | 5.6:1 | 4.29 | 41.39 | 5.48 | 13.15 | 41.31 | 54.54 |
| | H21 | 0.26 | 8.8:1 | 4.69 | 35.93 | 5.47 | 13.31 | 41.49 | 49.24 |
| | I21 | 0.26 | 14.1:1 | 5.05 | 31.01 | 5.44 | 13.79 | 41.63 | 44.8 |
| | J21 | 0.25 | 27.6:1 | 5.29 | 27.73 | 5.43 | 13.95 | 41.75 | 41.68 |
| | K21 | 0.25 | 1:0 | 5.31 | 27.46 | 5.4 | 14.42 | 41.88 | 41.88 |
| | water | 0.00 | — | 7.32 | 0.00 | 6.31 | 0.00 | 0.00 | 0 |
| Experiment 5 | I42 | 0.73 | 0:1 | 4.77 | 34.21 | 5.82 | 9.20 | 43.41 | 43.41 |
| | A42 | 0.59 | 0.9:1 | 4.51 | 37.79 | 5.73 | 10.61 | 47.53 | 48.4 |
| | B42 | 0.56 | 1.7:1 | 4.34 | 40.14 | 5.66 | 11.70 | 48.88 | 51.84 |
| | C42 | 0.52 | 4.2:1 | 4.41 | 39.17 | 5.41 | 15.60 | 50.43 | 54.77 |
| | H42 | 0.50 | 1:0 | 4.66 | 35.72 | 5.36 | 16.38 | 52.10 | 52.1 |
| | water | 0.00 | — | 7.25 | 0.00 | 6.41 | 0.00 | 0.00 | 0 |
| Experiment 6 | I42 | 0.73 | 0:1 | 5.05 | 31.01 | 5.73 | 10.61 | 41.62 | 41.62 |
| | D42 | 0.52 | 5.6:1 | 4.14 | 43.44 | 5.38 | 16.07 | 46.23 | 59.51 |
| | E42 | 0.51 | 8.8:1 | 4.53 | 38.11 | 5.41 | 15.60 | 46.50 | 53.71 |
| | F42 | 0.51 | 13.4:1 | 5 | 31.69 | 5.3 | 17.32 | 41.62 | 49.01 |
| | G42 | 0.50 | 28.2:1 | 5.11 | 30.19 | 5.31 | 17.16 | 46.86 | 47.35 |
| | H42 | 0.50 | 1:0 | 5.12 | 30.05 | 5.32 | 17.00 | 47.05 | 47.05 |
| | water | 0.00 | — | 7.32 | 0.00 | 6.41 | 0.00 | 0.00 | 0 |
| Experiment 7 | I63 | 1.10 | 0:1 | 5.48 | 25.85 | 5.86 | 12.14 | 37.99 | 37.99 |
| | A63 | 0.89 | 0.9:1 | 4.08 | 44.79 | 5.69 | 14.69 | 37.99 | 59.48 |
| | B63 | 0.84 | 1.7:1 | 3.97 | 46.28 | 5.69 | 14.69 | 42.23 | 60.97 |
| | C63 | 0.80 | 4.0:1 | 4.03 | 45.47 | 5.65 | 15.29 | 43.38 | 60.76 |
| | D63 | 0.78 | 5.5:1 | 4.26 | 42.35 | 5.55 | 16.79 | 43.69 | 59.14 |
| | E63 | 0.77 | 8.8:1 | 4.62 | 37.48 | 5.5 | 17.54 | 44.04 | 55.02 |
| | F63 | 0.76 | 13.7:1 | 5.24 | 29.09 | 5.41 | 18.89 | 44.27 | 47.98 |
| | G63 | 0.76 | 28.1:1 | 5.11 | 30.85 | 5.39 | 19.19 | 37.99 | 50.04 |
| | H63 | 0.74 | 1:0 | 5.58 | 24.49 | 5.32 | 20.24 | 44.73 | 44.73 |
| | water | 0.00 | — | 7.39 | 0.00 | 6.67 | 0.00 | 0.00 | 0 |

Example 3

Biofilm Prevention Performance of Compounds

Formulations A2-J2 as shown in Table 7 were made and tested in the biofilm prevention assay. The formulations were tested in an in-vitro static multi-treatment mixed species biofilm assay. Pellicle-coated peg lids were pre-treated with each formulation before biofilm growth. The treated peg lids were then inoculated with human whole saliva for 24 hours in order to grow a mixed species saliva-derived biofilm. This biofilm was treated with each formulation twice a day over the course of 60 hours, for a total of five 30-second treatments. The results are reported as log RLU and are shown in Table 7, with a lower value corresponding to less biofilm. The results were then used to create contour surfaces to maximize activity with varying concentrations of succinic acid and trans-aconitic acid. A positive control (Sample J2) comprised of a standard essential oil containing mouth rinse was also formulated and tested.

TABLE 7

Formulations to find synergies of SAA and tAA mixtures.

| Raw material | A2 | B2 | C2 | D2 | E2 |
|---|---|---|---|---|---|
| Succinic Acid | 0.21 | 0.21 | 0.25 | 0.12 | 0.037 |
| Aconitic Acid | 0.037 | 0.021 | 0.12 | 0.12 | 0.037 |
| Menthol | 0.038 | 0.038 | 0.038 | 0.038 | 0.038 |
| Thymol | 0.062 | 0.062 | 0.062 | 0.062 | 0.062 |
| Methyl Salicylate | 0.064 | 0.064 | 0.064 | 0.064 | 0.064 |
| Eucalyptol | 0.090 | 0.090 | 0.090 | 0.090 | 0.090 |
| Poloxamer 407 | 0.20 | 0.20 | 0.20 | 0.20 | 0.20 |
| Sodium Lauryl Sulfate | 0.20 | 0.20 | 0.20 | 0.20 | 0.20 |
| Benzoic Acid | 0.086 | 0.086 | 0.086 | 0.086 | 0.086 |
| Sodium Benzoate | 0.077 | 0.077 | 0.077 | 0.077 | 0.077 |
| Saccharin | 0.061 | 0.061 | 0.061 | 0.061 | 0.061 |
| Sucralose | 0.010 | 0.010 | 0.010 | 0.010 | 0.010 |
| Propylene Glycol | 7.0 | 7.0 | 7.0 | 7.0 | 7.0 |
| Sorbitol | 10.0 | 10.0 | 10.0 | 10.0 | 10.0 |
| FD&C Green #3 | 0.000037 | 0.000037 | 0.000037 | 0.000037 | 0.000037 |
| Flavor | 0.017 | 0.017 | 0.017 | 0.017 | 0.017 |
| Water | 81.8 | 81.7 | 81.7 | 81.8 | 82.0 |
| TOTAL | 100.0 | 100.0 | 100.0 | 100.0 | 100.0 |
| log RLU | 3.80 | 3.92 | 3.97 | 3.99 | 4.01 |

| Raw material | F2 | G2 | H2 | I2 | J2 |
|---|---|---|---|---|---|
| Succinic Acid | 0.12 | — | 0.037 | 0.12 | — |
| Aconitic Acid | — | 0.12 | 0.21 | 0.25 | — |
| Menthol | 0.038 | 0.038 | 0.038 | 0.038 | 0.038 |
| Thymol | 0.062 | 0.062 | 0.062 | 0.062 | 0.062 |
| Methyl Salicylate | 0.064 | 0.064 | 0.064 | 0.064 | 0.064 |
| Eucalyptol | 0.090 | 0.090 | 0.090 | 0.090 | 0.090 |
| Poloxamer 407 | 0.20 | 0.20 | 0.20 | 0.20 | 0.20 |
| Sodium Lauryl Sulfate | 0.20 | 0.20 | 0.20 | 0.20 | 0.20 |
| Benzoic Acid | 0.086 | 0.086 | 0.086 | 0.086 | 0.086 |
| Sodium Benzoate | 0.077 | 0.077 | 0.077 | 0.077 | 0.077 |
| Saccharin | 0.061 | 0.061 | 0.061 | 0.061 | 0.061 |
| Sucralose | 0.010 | 0.010 | 0.010 | 0.010 | 0.010 |
| Propylene Glycol | 7.0 | 7.0 | 7.0 | 7.0 | 7.0 |
| Sorbitol | 10.0 | 10.0 | 10.0 | 10.0 | 10.0 |
| FD&C Green #3 | 0.000037 | 0.000037 | 0.000073 | 0.000037 | 0.000037 |
| Flavor | 0.017 | 0.017 | 0.017 | 0.017 | 0.017 |
| Water | 82.0 | 82.0 | 81.8 | 81.8 | 81.8 |
| TOTAL | 100.0 | 100.0 | 100.0 | 100.0 | 100.0 |
| log RLU | 4.02 | 4.12 | 4.14 | 4.35 | 5.15 |

Note:
Sterile water control had log RLU of 7.39

What is claimed is:

1. An oral care composition comprising succinic acid, aconitic acid, and a carrier, said succinic acid and aconitic acid being present in the composition in a ratio of succinic acid to aconitic acid of from about 0.9:1 to about 14:1 by weight.

2. The composition of claim 1 having a ratio of succinic acid to aconitic acid of from about 0.9:1 to about 9:1.

3. The composition of claim 1 having a ratio of succinic acid to aconitic acid of from about 0.9:1 to about 6:1.

4. The composition of claim 1 having succinic acid and aconitic acid in a total combined amount of from about 0.1 to about 2% w/w of the composition.

5. The composition of claim 1 having succinic acid and aconitic acid in a total combined amount of from about 0.1 to about 1% w/w of the composition.

6. The composition of claim 1 having succinic acid and aconitic acid in a total combined amount of from about 0.1 to about 0.5% w/w of the composition.

7. The composition of claim 1 having succinic acid and aconitic acid in a total combined amount of from about 0.1 to about 0.3% w/w of the composition.

8. The composition of claim 1 wherein said carrier comprises water.

9. The composition of claim 8 wherein said carrier comprises a water/alcohol mixture.

10. The composition of claim 9 wherein said composition comprises alcohol in an amount of about 10% v/v or less by volume of the total composition.

11. The composition of claim 1 wherein said composition is free of alcohol.

12. The composition of claim 1 wherein said aconitic acid is trans-aconitic acid.

13. The composition of claim 1 wherein said composition further comprises at least one surfactant selected from the group consisting of anionic, non-ionic, cationic, amphoteric, zwitterionic surfactants, and combinations of two or more thereof.

14. The oral care composition of claim 13 further comprising at least one essential oil selected from the group consisting of thymol, eucalyptol, menthol, methyl salicylate, isomers of each of these compounds, and combinations of two or more thereof.

15. The oral care composition of claim 14, wherein said composition is in the form of a mouthwash, mouth rinse, toothpaste, gum, lozenge, or dissolvable strip.

16. The oral care composition of claim 15 wherein said composition is in the form of a mouthwash or mouthrinse.

17. The oral care composition of claim 16 wherein said composition is free of alcohol.

18. The oral care composition of claim 16 wherein said composition comprises succinic acid and trans-aconitic acid in a total combined amount of from about 0.1 to about 1% w/w of the composition.

19. The composition of claim 4 wherein said aconitic acid is trans-aconitic acid.

20. The composition of claim 5 wherein said aconitic acid is trans-aconitic acid.

\* \* \* \* \*